US010161225B2

(12) United States Patent
Jaffrey et al.

(10) Patent No.: US 10,161,225 B2
(45) Date of Patent: Dec. 25, 2018

(54) SEALS WITH EMBEDDED SENSORS (71) Applicant: Cameron International Corporation, Houston, TX (US)

(72) Inventors: Andrew Jaffrey, Oldmeldrum (GB); Brian Matteucci, Houston, TX (US); Edward C. Gaude, Tomball, TX (US)

(73) Assignee: Cameron International Corporation, Houston, TX (US)

( * ) Notice: Subject to any disclaimer, the term of this patent is extended or adjusted under 35 U.S.C. 154(b) by 303 days.

(21) Appl. No.: 14/933,200

(22) Filed: Nov. 5, 2015

(65) Prior Publication Data
US 2017/0130562 A1    May 11, 2017

(51) Int. Cl.
| | |
|---|---|
| *E21B 33/06* | (2006.01) |
| *E21B 41/00* | (2006.01) |
| *E21B 34/04* | (2006.01) |
| *G01L 1/24* | (2006.01) |
| *G01N 3/00* | (2006.01) |
| *E21B 33/035* | (2006.01) |
| *E21B 33/076* | (2006.01) |
| *G01L 1/22* | (2006.01) |
| *E21B 33/00* | (2006.01) |

(52) U.S. Cl.
CPC .......... *E21B 41/00* (2013.01); *E21B 33/0355* (2013.01); *E21B 33/061* (2013.01); *E21B 33/076* (2013.01); *E21B 34/04* (2013.01); *G01L 1/22* (2013.01); *G01L 1/242* (2013.01); *G01N 3/00* (2013.01); *E21B 2033/005* (2013.01)

(58) Field of Classification Search
CPC ........... G01L 1/242; G01N 3/00; E21B 41/00; E21B 33/061; E21B 34/04

USPC .................................................... 166/250.17
See application file for complete search history.

(56) References Cited

U.S. PATENT DOCUMENTS

| | | |
|---|---|---|
| 2,113,529 A | 4/1938 | Hild |
| 4,922,423 A | 5/1990 | Koomey et al. |
| 2002/0121369 A1 | 9/2002 | Allen |
| (Continued) | | |

FOREIGN PATENT DOCUMENTS

| | | |
|---|---|---|
| WO | 2014007790 A1 | 1/2014 |
| WO | 2015110478 A2 | 7/2015 |
| WO | WO-2015110478 A2 * | 7/2015 ........... E21B 33/085 |

OTHER PUBLICATIONS

Schotzko et al., "Embedded Strain Gauges for Condition Monitoring of Silicone Gaskets," Sensors 2014, 14(7), pp. 12387-12398, published by MDPI on Jul. 10, 2014.

(Continued)

*Primary Examiner* — Matthew R Buck
*Assistant Examiner* — Patrick F Lambe
(74) *Attorney, Agent, or Firm* — Helene Raybaud (57) ABSTRACT

An apparatus for monitoring the condition of a seal, such as a seal in a blowout preventer or in another oilfield device, is provided. In one embodiment, the apparatus includes a blowout preventer including a seal and a blowout preventer seal-monitoring system that includes a sensor positioned within a body of the seal and a data analyzer. The data analyzer has a processor and is configured to monitor a condition of the seal through analysis of data received by the data analyzer from the sensor positioned within the body of the seal. Additional systems, devices, and methods are also disclosed.

25 Claims, 9 Drawing Sheets

(56) References Cited

U.S. PATENT DOCUMENTS

| | | |
|---|---|---|
| 2004/0075218 A1 | 4/2004 | Heinzen |
| 2004/0083818 A1 | 5/2004 | Foote et al. |
| 2013/0153241 A1 | 6/2013 | Mallinson et al. |
| 2014/0174826 A1 | 6/2014 | Cayeux |
| 2015/0204182 A1 | 7/2015 | Andarawis et al. |
| 2015/0285054 A1 | 10/2015 | Johnson et al. |
| 2017/0009550 A1* | 1/2017 | Leuchtenberg ....... E21B 33/085 |

OTHER PUBLICATIONS

Jaffrey, U.S. Appl. No. 14/933,223, filed Nov. 5, 2015.
International Preliminary Report on Patentability for the equivalent International patent application PCT/US2016/060288 dated May 17, 2018.

* cited by examiner

SEALS WITH EMBEDDED SENSORS

BACKGROUND

This section is intended to introduce the reader to various aspects of art that may be related to various aspects of the presently described embodiments. This discussion is believed to be helpful in providing the reader with background information to facilitate a better understanding of the various aspects of the present embodiments. Accordingly, it should be understood that these statements are to be read in this light, and not as admissions of prior art.

In order to meet consumer and industrial demand for natural resources, companies often invest significant amounts of time and money in finding and extracting oil, natural gas, and other subterranean resources from the earth. Particularly, once a desired subterranean resource such as oil or natural gas is discovered, drilling and production systems are often employed to access and extract the resource. These systems may be located onshore or offshore depending on the location of a desired resource.

Further, such systems generally include a wellhead assembly mounted on a well through which the resource is accessed or extracted. These wellhead assemblies may include a wide variety of components, such as casings, hangers, blowout preventers, fluid conduits, pumps, and the like, that facilitate drilling or production operations. Wellhead assemblies typically include many seals for containing fluid pressure. Examples of such seals include ram top seals, ram packers, annular packers, gaskets, and O-rings. These seals wear during use and may be replaced after failure or on a regularly scheduled basis.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Embodiments of the present disclosure generally relate to sensors for measuring the condition of seals, such as those found in wellhead assemblies or other oilfield components. For instance, various embodiments described below include sensors embedded in seals for acquiring data that can be used to determine and monitor the condition of the seals. The acquired data may include measurements of physical operating conditions, such as measurements of temperature, stress, or strain experienced by the seal. In some embodiments, sensors are provided as wires embedded in elastomeric seals and the acquired data includes electrical measurements from the wires, which can be analyzed to determine seal condition. While seal data acquired with the sensors can be used for condition-based monitoring, the data could be used for other purposes, such as for predictive maintenance, controlling operation of a wellhead assembly component (e.g., a blowout preventer), or tracking objects (e.g., drill string tool joints) passing through a wellhead assembly.

Various refinements of the features noted above may exist in relation to various aspects of the present embodiments. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. Again, the brief summary presented above is intended only to familiarize the reader with certain aspects and contexts of some embodiments without limitation to the claimed subject matter.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings, wherein.

DETAILED DESCRIPTION OF SPECIFIC EMBODIMENTS

Specific embodiments of the present disclosure are described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not require any particular orientation of the components.

Figures 1, 2, 3:
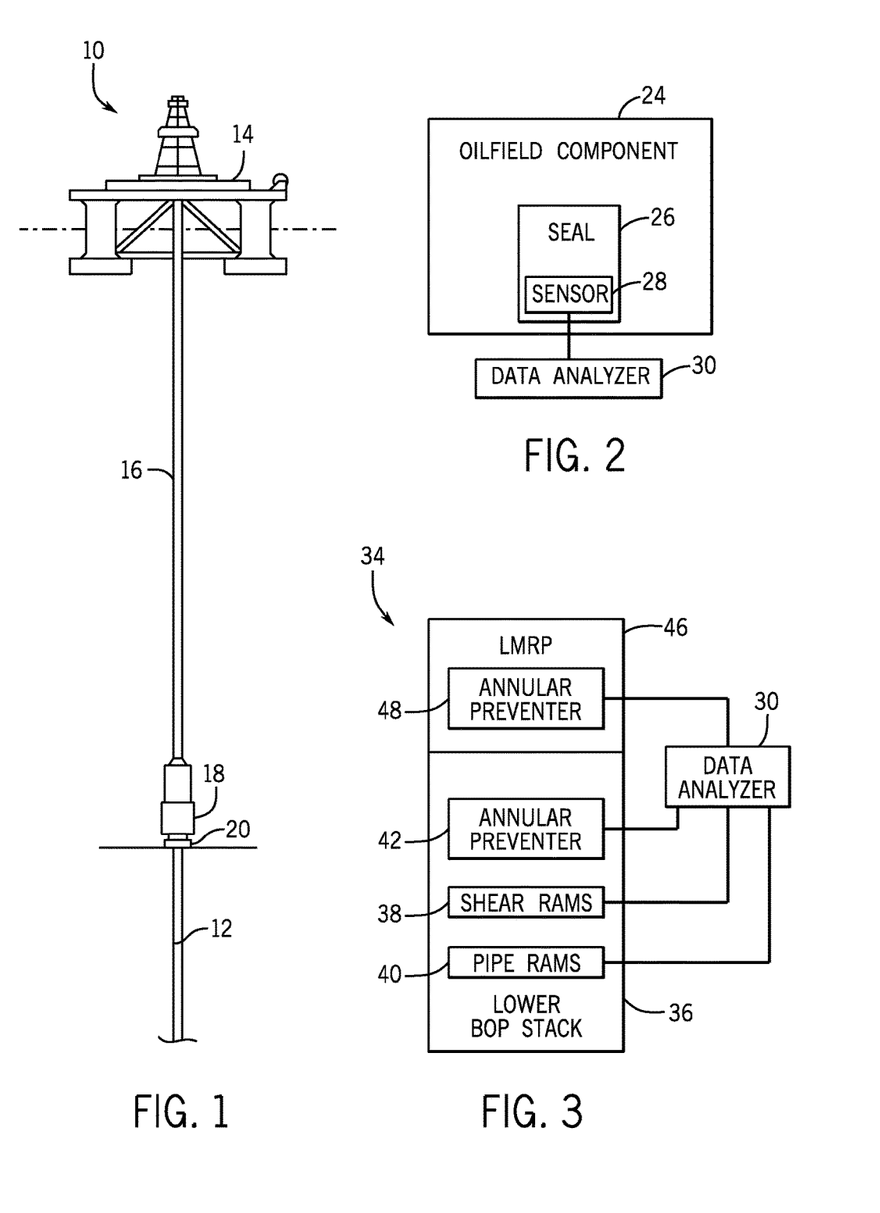
FIG. 1 generally depicts a well apparatus in the form of an offshore drilling system with a drilling rig coupled by a riser to a wellhead assembly in accordance with one embodiment of the present disclosure.
FIG. 2 is a block diagram of a seal-monitoring system including a seal of an oilfield component, the seal having a sensor for measuring operating data, and a data analyzer for processing the operating data collected by the sensor in accordance with one embodiment.
FIG. 3 depicts a blowout preventer stack assembly having various components with seals having sensors for measuring operating data that may be used for condition-based monitoring in accordance with one embodiment.

Turning now to the present figures, a well apparatus 10 is illustrated in FIG. 1 in accordance with one embodiment. The apparatus 10 (e.g., a drilling system or a production system) facilitates access to or extraction of a resource, such as oil or natural gas, from a reservoir through a well 12. The apparatus 10 is generally depicted in FIG. 1 as an offshore drilling apparatus including a drilling rig 14 coupled with a riser 16 to a wellhead assembly 18 installed at the well 12. Although shown here as an offshore system, the well apparatus 10 could instead be an onshore system in other embodiments.

As will be appreciated, the drilling rig 14 can include surface equipment positioned over the water, such as pumps, power supplies, cable and hose reels, control units, a diverter, a gimbal, a spider, and the like. Similarly, the riser 16 may also include a variety of components, such as riser joints, flex joints, a telescoping joint, fill valves, and control units, to name but a few. The wellhead assembly 18 includes equipment, such as blowout preventers, coupled to a wellhead 20 to enable the control of fluid from the well 12. Any suitable blowout preventers could be coupled to the wellhead 20, such as ram-type preventers and annular preventers. The wellhead 20 can also include various components, such as casing heads, tubing heads, spools, and hangers.

The drilling rig 14, the riser 16, and the wellhead assembly 18 include various oilfield components having seals for containing fluid pressure. Seals of blowout preventers and other oilfield components are prone to failure owing to age, degradation of material, abuse, excessive pressure, excessive stresses, extremes of temperature, wear, and myriad other influences. In some instances, seals are replaced on a scheduled basis (e.g., after a pre-defined time, cycle count, or event) regardless of condition. In at least the case of blowout preventers, such replacement frequently requires considerable time and effort given the nature of the blowout preventer equipment and the steps necessary to access the seals for replacement. The blowout preventer is necessarily out of commission while such work is performed. Seals are also replaced when they are known to have failed. This will often be following a potentially lengthy investigation to diagnose the source of a leak.

The physical properties of a seal can vary with operating conditions, such as environmental conditions (e.g., temperature) and forces (e.g., stress and strain) experienced by the seal. Traditionally, the seals used throughout a blowout preventer and in other oilfield components are simply shaped pieces of material. These traditional seals are not intelligent, do not provide feedback, and are not capable of reporting their health or the operating conditions they have been exposed to.

In accordance with at least certain embodiments of the present disclosure, however, oilfield components are provided with "smart" seals having embedded sensors that enable the acquisition of data relevant to the seals and their operation from the seals themselves. The acquired data can be used for condition-based monitoring and predictive maintenance, among other things. A simple example of an oilfield component 24 having a seal 26 with an embedded sensor 28 is generally depicted in FIG. 2. Various examples of oilfield components with such smart seals having sensors are described in greater detail below, but it will be appreciated that oilfield components 24 and their seals 26 may take many different forms in addition to those described below. In at least some embodiments, the seal 26 is an elastomer seal having the embedded sensor 28. The seal 26 can include a ram packer, a ram top seal, an annular packer, an O-ring, a gasket, a pressure seal, a wiper seal, or a shaft seal, to name just some examples. In some embodiments, the seals 26 include local power generation and communications, as further described below.

The types of data acquired with sensors in the seals may vary depending on the location and importance of the seals. In some embodiments, the smart seals measure actual forces or environmental conditions experienced by the seals. For example, sensors 28 can be used to measure temperature or pressure experienced by the seals. The sensors 28 are provided as fiber-optic sensors in certain embodiments. The influence of temperature and pressure on the seal will, in turn, influence the properties of the embedded optical fibers of the sensors and, with suitable experimental calibration, will give rise to an indication of physical conditions experienced by the seal. In the case of blowout preventers, the physical conditions experienced by the seal can be determined from the sensor data during its operating cycle (including stationary phases when the blowout preventer is fully open or fully closed). Sensors 28 may also or instead be provided as strain gauges embedded in the bodies of smart seals 26 to measure stress and strain (which may include shear) experienced by the seals. The strain gauges could be single-axis or multi-axis strain gauges, and in one embodiment the sensors 28 include multiple single-axis strain gauges embedded within a smart seal in a multi-axis configuration.

By recording such data and comparing with baseline data for similar seals including, for example, the manufacturer's specifications and recommended operating conditions for the type of seal, or empirical data from a deployed population of such seals, the user can be alerted to instances where the forces exerted on a seal have been measured to be beyond those recommended by the baseline data. This information may be useful in the context of condition-based monitoring and predictive maintenance.

Another measurement that can be considered in at least certain embodiments is fluid ingress. If the ingress of fluid is detected within the seal itself (via the embedded sensor) this may suggest a leak or degradation of the seal material. In either case, the operator can be alerted to the need for further investigation and potential remedial action. In further embodiments, sensors embedded within smart seals can detect the presence of specific chemicals within the seal.

In situations where smart seals are used with dynamic components (e.g., blowout preventer rams) such that the seal travels along another component (or another component travels past the seal), and depending on the other data available (e.g., speed and time of movement), the stress experienced by the seal can be used to determine what the degree of friction is in the bore. This might indicate a build-up of unwanted material, the deterioration of the surface of the bore owing to say, galling, or some other issue that merits investigation. High friction will, among other things, increase the wear on the seal and could require it to be replaced sooner than expected. In one embodiment, friction on a seal due to relative motion of the seal and another component is determined from stress measured with a sensor embedded in the seal. The determined amount of friction can be compared with a friction threshold (e.g., an expected friction level or maximum desired friction level) and an operator can be alerted if the determined amount of friction exceeds the threshold amount. Trends in data acquired with the seal sensors can also be monitored over time to facilitate condition-based-monitoring.

Depending on the nature of the sensor and the one or more measurements to be made, it may be desirable to embed multiple sensors in a single seal (e.g., to provide distributed sensing coverage throughout the seal). For example, small, area-focused sensors (such as strain gauges) could be embedded at multiple locations within a seal, whereas others (such as fiber-optic sensors) may span the length of a seal.

From the above, it will be appreciated that monitoring either or both the environmental conditions and the actual forces experienced by seal components with embedded sensors enables a more holistic approach to seal condition monitoring and replacement. A seal-monitoring system for a blowout preventer (or for another apparatus) can include one or more smart seals 26 and a data analyzer 30 for processing data acquired with the smart seals 26. In some embodiments, the data analyzer 30 compares data acquired with the smart seals (e.g., stresses and temperatures experienced by the seals) to appropriate baseline data and uses predictive algorithms to calculate an expected performance characteristic for the seals. The expected performance characteristic could be an expected longevity of a seal based on the experienced conditions. It will be appreciated that the expected longevity could be expressed in different ways, such as an estimated remaining service life or a total expected length of service.

In some cases, this analysis may suggest replacement of seals earlier than either cycle count or elapsed time would suggest. Such a suggestion may be in response to harsh operating conditions or misuse, for example, and may prevent unplanned downtime (perhaps pulling the whole blowout preventer, thus incurring millions of dollars of lost revenue) or possible failure of the equipment to operate as designed when required (e.g., to prevent a blow-out). In other cases, analysis of the data acquired with sensors of the smart seals may indicate that the seals could be replaced much later than ether cycle count or elapsed time would suggest. This delayed maintenance may save equipment operators significant amounts of time and allow these operators to delay expenditure associated with the maintenance.

The data analyzer 30 can receive and analyze smart seal data from multiple components. By way of example, the data analyzer 30 is generally depicted in FIG. 3 as being coupled (e.g., via wired or wireless connections) to receive data from seals of various components of a subsea blowout preventer stack assembly 34. The stack assembly 34 includes a lower blowout preventer stack 36 that can be coupled above the wellhead 20. The lower blowout preventer stack 36 includes ram-type preventers (e.g., represented as shear rams 38 and pipe rams 40) and an annular preventer 42. The blowout preventer stack assembly 34 is further shown in FIG. 3 as including a lower marine riser package (LMRP) 46 having an annular preventer 48.

The data analyzer 30 can process the data acquired by smart seals of the stack assembly 34 (e.g., of the shear rams 38, the pipe rams 40, and the annular preventers 42 and 48), such as to determine seal condition. The data analyzer 30 could be positioned near one or more components having a seal with an embedded sensor (e.g., as part of the stack assembly 34), or could be provided remote from any such smart seals. In one subsea embodiment, the data analyzer 30 is provided at the surface on the drilling rig 14. The data acquired by the smart seals could also or instead be transmitted to other locations for processing, such as to an onshore processing site remote from the drilling rig 14. Further, the data analyzer 30 could be provided as part of a system for monitoring the condition and operation of other components (e.g., a system for monitoring operation of a blowout preventer stack).

It will be appreciated that the lower blowout preventer stack 36 and the LMRP 46 can include other components in addition to or in place of those depicted in FIG. 3. The LMRP 46, for example, can include control pods for controlling operation of the preventers of the lower blowout preventer stack 36 and the LMRP 46. Additionally, in some embodiments (e.g., onshore embodiments) the LMRP 46 is omitted from the blowout preventer stack assembly 34.

A bore through the blowout preventer stack assembly 34 allows objects, such as a drill string, to pass into the well 12. The drill string and other objects may routinely pass through the bore of the blowout preventer stack assembly 34 during normal operations. Examples of other objects that may pass through the stack assembly 34 include reamers, downhole assemblies, running tools, and other tools. As discussed in greater detail below, a component of the stack assembly 34 (e.g., the annular preventer 42) can have a smart seal with an embedded sensor that enables the detection of objects (e.g., drill string tool joints) passing through the component. This detection (e.g., by the data analyzer 30 through analysis of data from the embedded sensor) can be used for tracking the objects and controlling operation of the component.

Various components can be used to facilitate data acquisition with the smart seals 26. For instance, in FIG. 4, a data acquisition system 60 is generally depicted as including a power supply 64, one or more sensors 66, data storage 68 (e.g., a memory device), a processor 70, and one or more communications devices 72. The data acquisition system 60 could include other components in addition to, or in place of those depicted in FIG. 4. The various components can be operatively coupled to one another in any suitable manner to facilitate electrical communication (e.g., of power, measurement data, communications, and control signals), such as with one or more shared buses 74.

Figure 4:
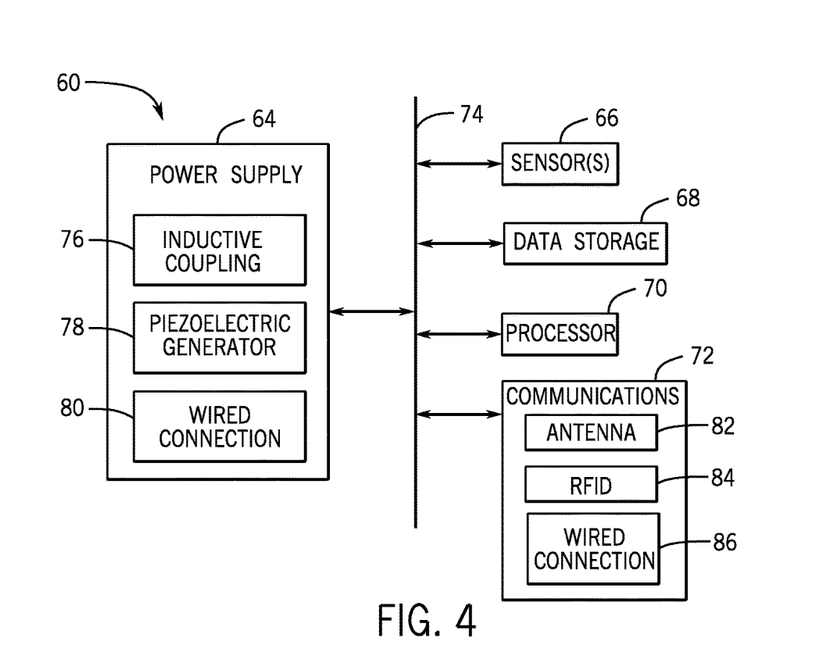
FIG. 4 is a block diagram of a data acquisition system for obtaining seal data in accordance with one embodiment.

Components of the data acquisition system 60 can be embedded in the body of a seal to facilitate measurement of various operational data, such as measurements of environmental conditions or forces experienced by the seal. While a smart seal 26 may include a sensor 66 as the embedded sensor 28, the smart seal 26 may also include other components embedded in the body of the seal 26. For instance, any or all of a power supply 64, data storage 68, processor 70 (or other control circuitry), and a communications device 72 could also be embedded within the body of the seal 26. With careful choice of materials and the use of very small components it may be possible to manufacture seals that display the same mechanical properties as those manufactured without embedded devices. As one example of this, by using a material for a sensor substrate that is chemically similar to the host material, the bonding between the embedded component and the host material is maximized.

Depending on where the seal is fitted within a blowout preventer (or within some other component), there are multiple options for providing power to the sensors embedded in it. Three examples of these options are depicted in FIG. 4 as an inductive coupling 76, a piezoelectric generator 78, and a wired connection 80. It will be appreciated that the power supply 64 could be provided in any one of these forms, in a different form (e.g., a battery), or in any combination of suitable forms. In some instances, a seal 26 has an exposed edge that allows direct connection of wires to trailing leads from the sensor. In other instances, such as with seals internal to a component, local power generation within the seal 26 may be desirable. The seal 26 in one embodiment uses an inductive coupling 76 having a close-proximity but non-contact connection between the primary and secondary elements (e.g., coils) of an inductive coupler. The secondary element of the inductive coupler can be embedded within the seal body, while the primary element is provided in close proximity outside the seal. In other embodiments, a piezoelectric generator 78 embedded in the seal 26 may be used to provide power to the other electronic components in the seal. In one example of the generator 78, pressure from a local source (e.g., control fluid or wellbore fluid) is harnessed to deform a piezoelectric element, thus generating electrical energy. This energy can be stored in a capacitor to act as a battery for the embedded electrical components (e.g., the sensor 66).

There are also various options for communicating with sensors embedded in seals 26. By way of example, a seal 26 could include one or more of an antenna 82, a radio-frequency identification (RFID) tag 84, or a wired connection 86 to enable communication between components embedded within the seal and an external system (e.g., an external data analyzer 30). The particular device or devices used for communication may depend on the accessibility of the seal 26 in the component 24. If the seal 26 has an exposed edge, a wired connection 86 may be used (e.g., with direct connection of wires to trailing leads from the sensor). If the seal is internal to the component 24, then any suitable wireless approach may be used. For example, an approach based on RFID (e.g., using an RFID tag 84) could be used to communicate with the antenna 82 embedded in the seal 26 along with the one or more sensors 66 being read.

The retrieval of data acquired with embedded sensors 66 might be performed in real-time, in pseudo real-time, or on a batch basis. In one embodiment, the sensor remains in communication with an external data receiver (e.g., of the data analyzer 30) and the real-time approach will report each reading by the sensor as it is made. In another embodiment, the pseudo real-time approach will report each reading shortly after it is made. This allows the sensor to be out of communication with the receiver at the time the reading is made, and to reestablish communication and transmit the sensor reading shortly thereafter. As discussed more particularly below with reference to FIG. 15, one example of this would be where the sensor reading is made at the end of the travel of a ram, where the elements of the communications link (e.g., the antenna 82 and the external receiver) are too far apart. When the ram travels back to its default position, however, the elements of the communications link are close enough to function. In a further embodiment, the batch-basis approach will provide for the batch download of data from a storage device (e.g., the data storage 68) associated with one or more embedded sensors of a smart seal. This approach could be adopted where sensors are in particularly hard-to-reach locations or where the nature of the monitoring is such that it is acceptable to simply download the data on an irregular basis. In some instances, a smart seal of a component may alternate between communicating in real-time, in pseudo real-time, or on a batch basis.

The nature of the seals in a blowout preventer assembly is such that it may not be necessary to retrieve the information in real-time. As long as the data are gathered and transmitted to the operator on a regular basis (e.g., daily), then the trends and likely effects of extreme conditions can be brought to the operator's attention. It will be appreciated, however, that the information could be retrieved in real-time in some embodiments. Depending on the location and nature of a smart seal of a subsea blowout preventer stack, it might be useful (or even necessary, in some instances) to download and process the data when the blowout preventer stack is returned to the drilling rig for servicing. In this situation, the data on seal performance will allow maintenance personnel to make informed decisions as to which seals to replace, inspect, or ignore.

In some embodiments, it might not be possible to provide all sensors with sufficient on-going energy to maintain the operation of a clock. In such cases, the data may be written to the local data storage device 68 in chronological order. While it may not then be possible to plot a trend against a specific time, trends will still be visible, such as a detected increase in fluid ingress or ongoing exposure to high shear strains that indicate likely premature failure of the seal.

Recording of data measured by embedded sensors of smart seals may be omitted in those cases where the data are recorded in real-time or pseudo real-time, since these cases imply an adequate communications link to retrieve the data. In some such instances, the data are time stamped at the point of reception by the communications device (a receiver of the data analysis system 30) and will allow correlation between the seal (sensor) data and other events related to blowout preventer operations (e.g., commands to close a ram). Being able to superimpose such data in a flexible manner on the user's interface may allow for powerful insights into how the equipment behaves under a range of operating conditions.

Figure 5:
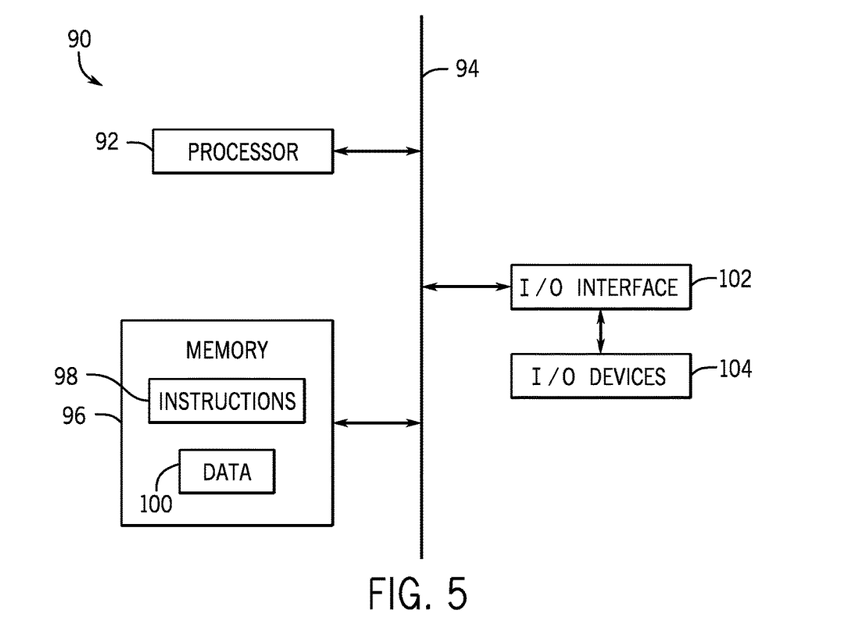
FIG. 5 is a block diagram of a programmable data analyzer that can be used for condition-based monitoring in accordance with one embodiment.

It is noted that the data analyzer 30 for implementing various functionality described herein can be provided in any suitable form. In at least some embodiments, such a data analyzer 30 is provided in the form of a processor-based system, an example of which is illustrated in FIG. 5 and generally denoted by reference numeral 90. In this depicted embodiment, the system 90 includes a processor 92 connected by a bus 94 to a memory device 96. It will be appreciated that the system 90 could also include multiple processors or memory devices, and that such memory devices can include volatile memory (e.g., random-access memory) or non-volatile memory (e.g., flash memory and a read-only memory). The one or more memory devices 96 are encoded with application instructions 98, such as software executable by the processor 92 to analyze data from smart seals for condition-based monitoring, predictive maintenance, seal friction determination, blowout preventer control, or object tracking, or to provide other functionality described herein. Data 100 (e.g., seal manufacturer's specifications and recommended operating conditions, other baseline data) may also be stored in memory devices 96. In one embodiment, the application instructions 98 are stored in a read-only memory and the data 100 are stored in a writeable non-volatile memory (e.g., a flash memory).

The system 90 also includes an interface 102 that enables communication between the processor 92 and various input or output devices 104. The interface 102 can include any suitable device that enables such communication, such as a modem or a serial port. In at least some embodiments, the interface 102 includes a wireless data receiver for receiving data from smart seals. The input and output devices 104 can include any number of suitable devices. For example, in one embodiment the devices 104 include smart seals 26, and data transmitted from the smart seals 26 can be analyzed with the processor 92 for condition-based monitoring. The devices 104 could also include a keyboard to allow user-input to the system 90 and a display or printer to output information from the system 90 to a user.

Figure 6:
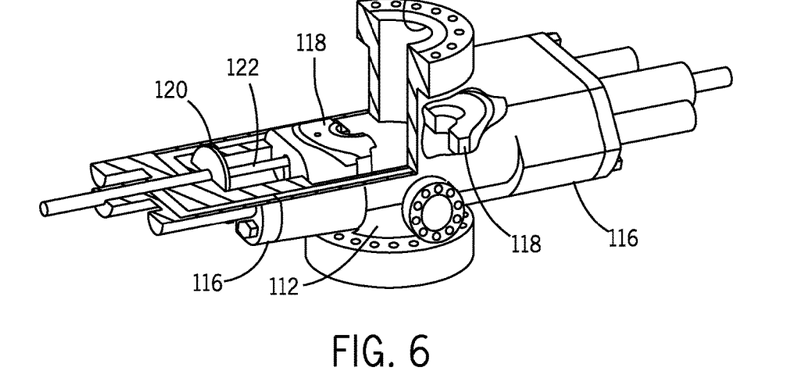
FIG. 6 depicts a blowout preventer having various seals in accordance with one embodiment.

Additional embodiments with smart seals 26 having embedded sensors are depicted in FIGS. 6-19 and described below. It will be appreciated, however, that smart seals with embedded sensors can be used in a variety of other components and arrangements. By way of example, a blowout preventer 110 with smart seals is depicted in FIG. 6. The blowout preventer 110 includes a body 112, a bore 114 that enables passage of fluid or tubular members through the blowout preventer 110, and bonnet assemblies 116 mounted to the body 112. Each ram 118 inside the blowout preventer 110 is moved into or out of the bore 114 by an associated piston 120 and connecting rod 122 of a bonnet assembly 116. In the presently illustrated embodiment, the connecting rod 122 includes a button received in the ram 118 to allow the connecting rod 122 to push or pull the ram 118 within the blowout preventer 110.

Figure 7:
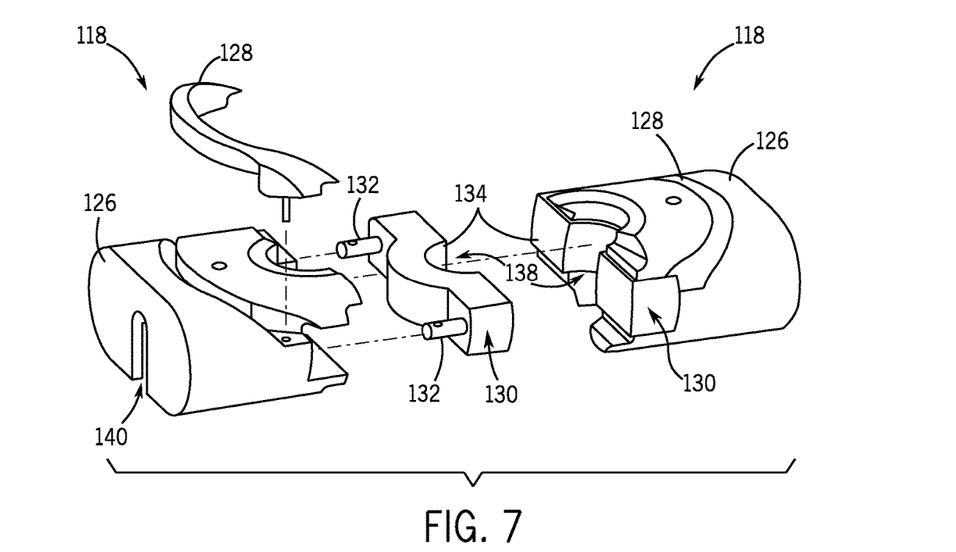
FIG. 7 depicts two rams of the blowout preventer of FIG. 6 in additional detail in accordance with one embodiment.

The rams 118 are depicted as pipe rams in FIG. 6, and are shown in greater detail in FIG. 7. Each ram 118 includes a body or ram block 126, a ram seal 128 (shown as a top seal in FIG. 7), and a ram packer 130. The ram seal 128 and the ram packer 130 include elastomeric materials that facilitate sealing by the ram 118 within the blowout preventer 110. The ram packer 130 includes alignment pins 132 that may be received in corresponding slots of the ram block 126 when the ram packer 130 is installed. The ram packers 130 include an elastomeric body 134 and recesses 138 that allow a pair of opposing rams 118 to close about and seal against a tubular member (e.g., drill pipe). The recesses 138 may be sized according to the diameter of the pipe about which the packers 130 are intended to seal. Additionally, in other embodiments, the rams 118 could be provided as variable-bore pipe rams used to seal around pipes within a range of diameters. Each ram 118 also includes a slot 140 for receiving a portion (e.g., a button) of a connecting rod 122, as discussed above.

Figure 8:
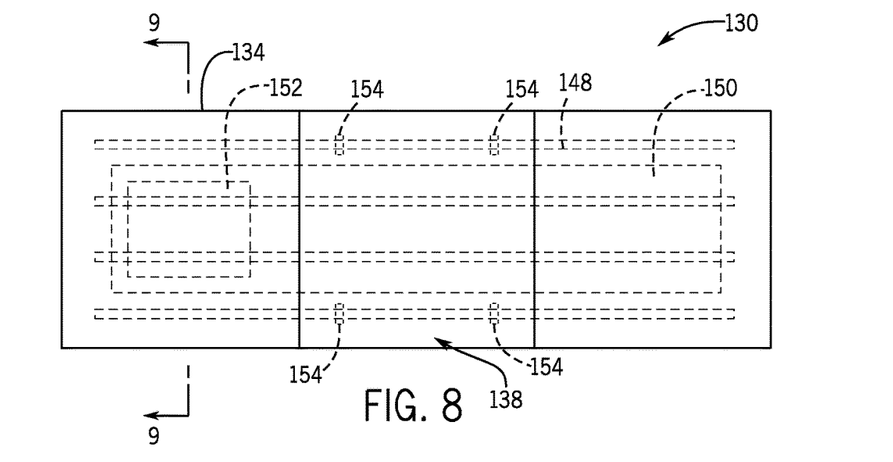
FIGS. 8 and 9 depict a ram packer with sensors for collecting operating data for the packer in accordance with one embodiment.
Figure 9:
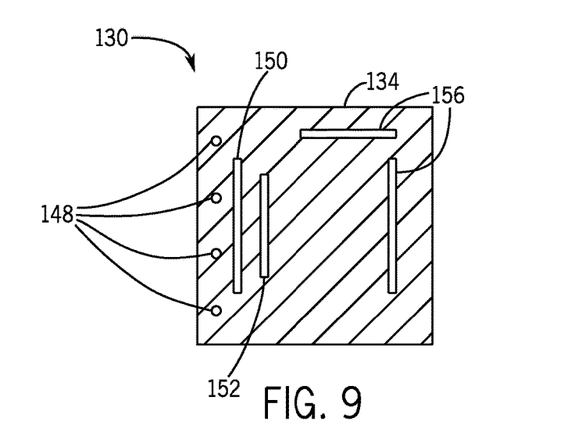

The ram seals 128 and the ram packers 130 can be provided as smart seals with any desired number, type, and arrangement of embedded sensors. In FIGS. 8 and 9, a ram packer 130 is shown as having fiber-optic sensors 148 embedded in its elastomeric body 134. The fiber-optic sensors 148 are provided near the contoured front face of the packer 130 designed to seal around an object in the bore of the blowout preventer 110 and to close against an opposing ram packer 130. The fiber-optic sensors 148 may run parallel to the front face of the packer 130 and follow the contour of the front face (including bending near the middle of the sensors to accommodate the recess 138). The depicted ram packer 130 also includes a power supply 150, electronics 152, and strain gauges 154 embedded in the elastomeric body 134. The power supply 150 can be provided in any suitable form (e.g., a piezoelectric generator 78), and the electronics 152 may include various circuitry that facilitates operation of the smart seal (e.g., data storage 68, processor 70, and communications circuitry). An antenna 156 (e.g., an RFID antenna) can also be embedded in the elastomeric body 134 for communications. Two orientations of the antenna 156 are shown in FIG. 9. While the packer 130 could include two separate antennas 156 (e.g., for redundancy and to improve throughput), it will be appreciated that a single antenna 156 could instead be used (in either orientation shown in FIG. 9, or in some other orientation).

Figure 10:
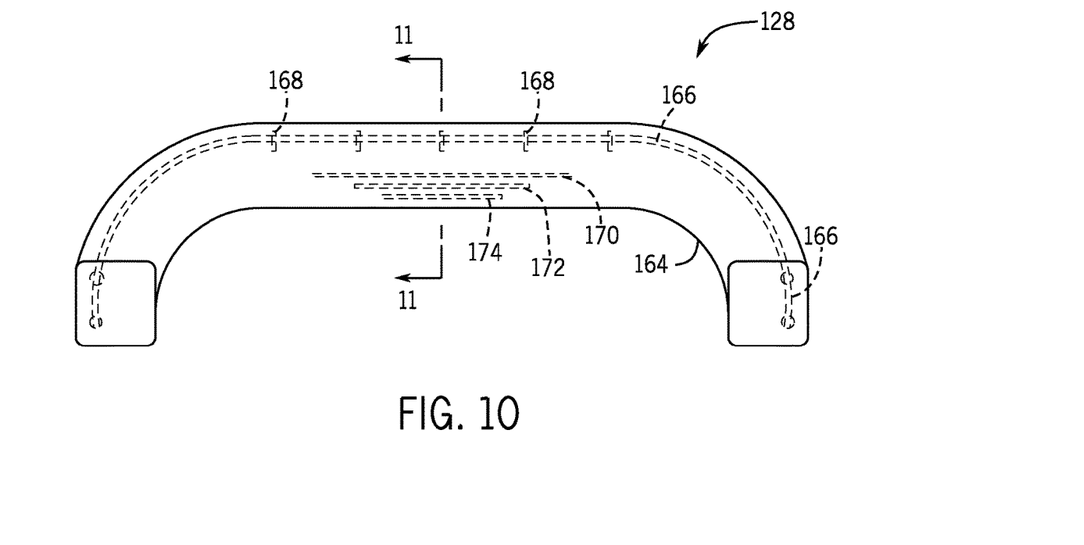
FIGS. 10 and 11 depict another ram seal with sensors for collecting operating data for the seal in accordance with one embodiment.
Figure 11:
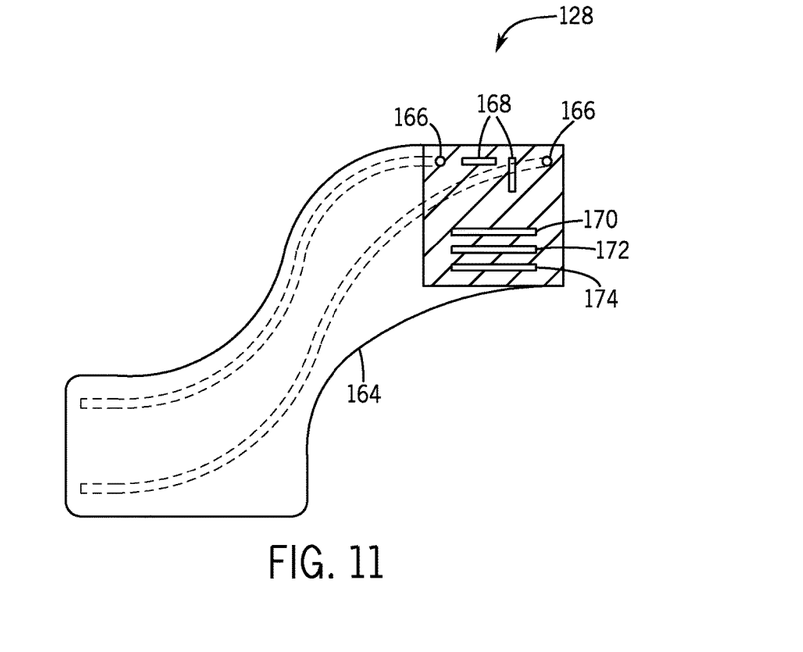

An example of a ram seal 128 with smart seal functionality is generally illustrated in FIGS. 10 and 11. As depicted here, the ram seal 128 includes fiber-optic sensors 166 and strain gauges 168 embedded in an elastomeric body 164. In at least one embodiment, and as generally shown in FIG. 11, the strain gauges 168 include single-axis strain gauges provided in different orientations so as to function collectively as a multi-axis strain gauge. The ram seal 128 of this embodiment also includes a power supply 170 (e.g., a piezoelectric generator), a communications antenna 172 (e.g., an RFID antenna), and electronics 174 (e.g., data storage 68, processor 70, and communications circuitry).

The ram seals 128 travel with the rams as they close and open the bore through the blowout preventer. At a minimum they are subject to wellbore pressure, friction, and drilling mud. The pressure on the forward face of the seal is not necessarily always equal to the pressure on the back face of the seal, exacerbating the stresses and strains experienced by the seal. By embedding sensors in the ram seals, these stresses and strains can be measured, quantified, and the likely impact on the longevity of the seals considered from a factual perspective—including, in at least some cases, the temperature of the seal when the forces were experienced.

By making measurements such as these, and also the detection of fluid ingress, operators can be alerted to potential issues before they become problematic. Through such monitoring, maintenance schedules can become proactive rather than reactive. Further, downtime caused by unnecessary maintenance activities may be reduced, as may downtime caused by unexpected failures.

As with the ram seals 128, the sensors embedded in the ram packers 130 (e.g., fiber-optic sensors 148 and strain gauges 154) can be used to acquire various operational data (e.g., temperatures, stresses, and strains experienced by the ram packers 130) and to optimize maintenance scheduling while minimizing downtime. Unlike the ram seals 128, however, the ram packers 130 are intended to have direct force applied to their front faces. This, along with other properties such as deformation, provides additional insights into not just the health of the ram packer 130, but also its performance. If a ram is closed and left for a period, the packer material may respond to changes in temperature, to pressure from the wellbore material, from other fluids in the blowout preventer cavity, and from the natural processes of deformation and relaxation associated with the material. In such situations it might not be the case that the changes are sufficient to cause a reduction in sealing efficiency, but by embedding sensors in the packer the data can be made available to the system operator in order that unexpected trends can be identified and remedial action taken as necessary.

One example of this might be where the ram has been closed and locked, but where there is a leak on the closing side of the piston, in which case the holding force of the ram is diminishing over time. Depending on the instrumentation fitted to the closing mechanism, this reduction in holding pressure might not be detected. A sensor-enabled packer, however, could provide data that would allow the operator to infer that something was wrong somewhere in the closing circuit. If the ram is confirmed to be locked, then a possible cause of relaxation of the measured force on the packer could be leakage on the closing side of the piston. This example illustrates one of the benefits of taking a more holistic approach to blowout preventer monitoring by allowing measurements made for one component to be used in the diagnosis of problems in other components.

Figure 12:
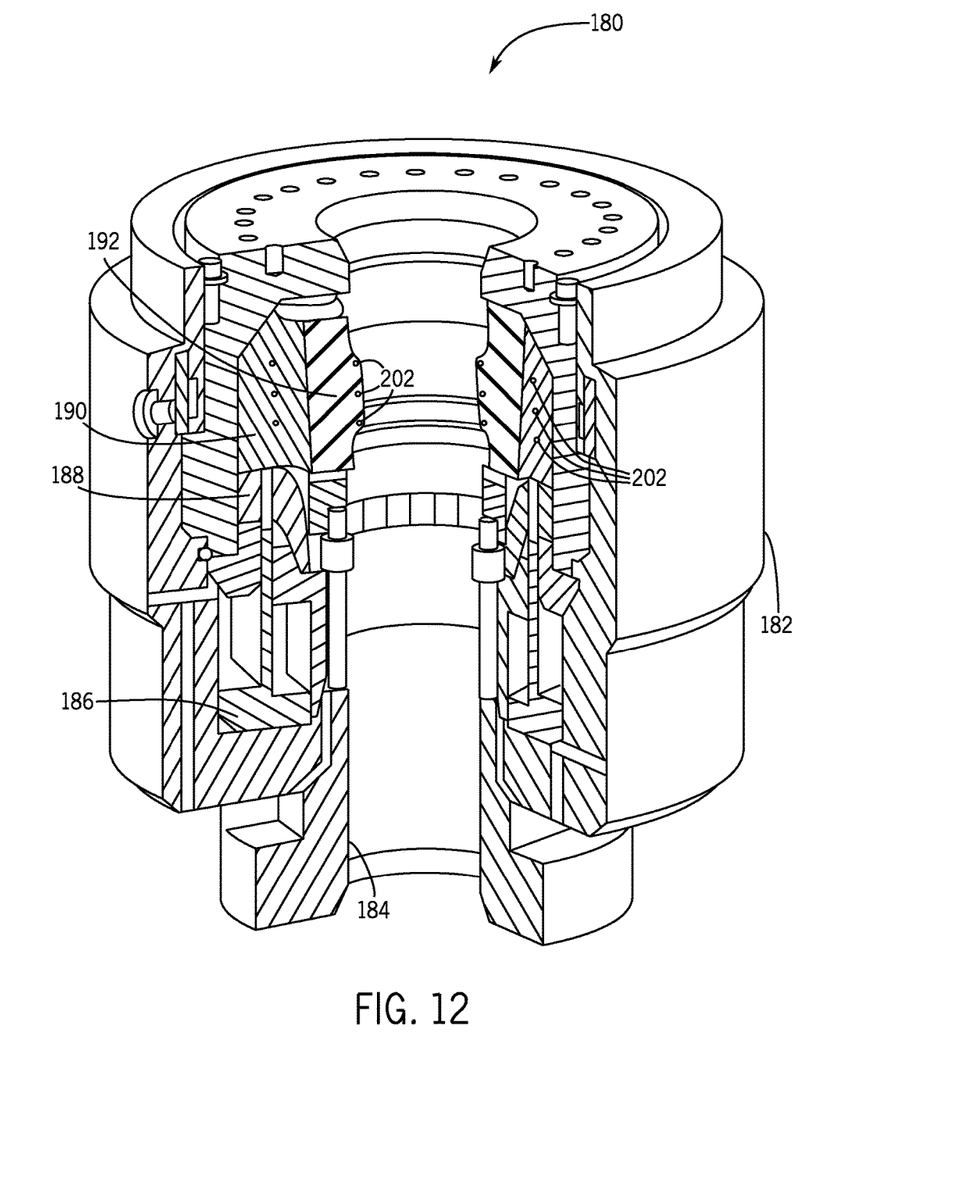
FIG. 12 depicts an annular blowout preventer having various sealing components with embedded sensors in accordance with one embodiment.

Another example in which sensor-enabled elastomers could provide useful information is in annular blowout preventers. One example of an annular blowout preventer 180 is generally depicted in FIG. 12. The annular blowout preventer 180 includes a hollow body 182. Drill strings, tools, and other objects may be passed through a bore 184 in the body 182. As shown, the annular blowout preventer 180 includes a piston 186 and a pusher plate 188 that engages a donut 190. Closing pressure forces the piston 186 and the pusher plate 188 upward, which compresses the donut 190 and causes the donut 190 to push the packer 192 radially inward to seal the bore 184. In at least some embodiments, the donut 190 and the packer 192 have elastomeric bodies. The closed packer 192 can seal around an object (e.g., a drill string) in the bore 184 or, in at least some instances, can seal an open bore.

Sensors can be embedded in any of the sealing components of the annular blowout preventer 180, such as in seals themselves (e.g., the packer 192) or in other components that facilitate sealing (e.g., the donut 190). As shown in FIG. 12, sensors 202 are embedded in the donut 190 and the packer 192. The sensors 202 of some embodiments include fiber-optic sensors, but other sensors (e.g., such as strain gauges or sensing wires) could be used in addition to, or in place of such fiber-optic sensors. Although not shown in FIG. 12, it will be appreciated that other components may also be embedded in the donut 190 and the packer 192, such as power supplies, memory devices, processors, and communication devices.

By embedding sensors in either or both the donut 190 and the packer 192, the working experience of the annular blowout preventer 180 becomes a matter of record, rather than of speculation. The techniques to be applied and the benefits derived from such measurements may be similar to those of the ram packer, but whereas the ram packer is a semi-circular, half-torus unit, the annular blowout preventer packer 192 and donut 190 are circular. This offers different opportunities for the types of sensors to be used and the means of providing power and communications to those sensors. The annular packer 192 and donut 190 do not travel in the same way that a ram seal or a ram packer does, so there is greater scope for wired connections rather than reliance on non-contact techniques, such as those discussed herein.

Figure 13:
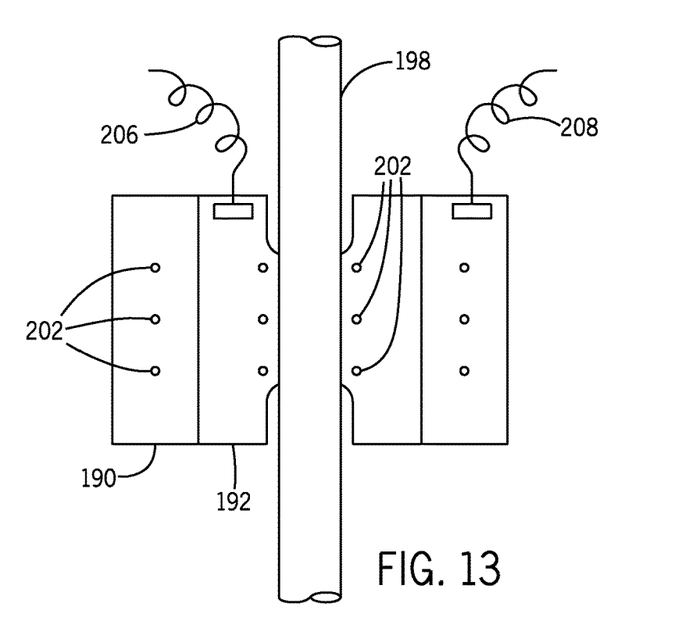
FIGS. 13 and 14 generally depict a packer of an annular preventer closed about different portions of a drill string in accordance with one embodiment.
Figure 14:
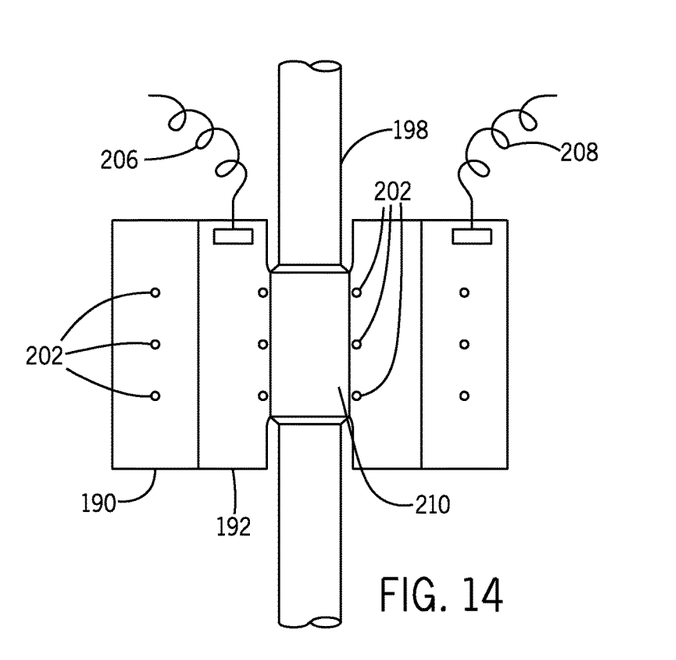

An annular blowout preventer is often subject to tool joints of a drill string (or other objects) being dragged through its packer. For example, an annular packer 192 can be closed about a drill string 198, as generally shown in FIG. 13. The donut 190 and the packer 192 are depicted here as including wired connections 206 and 208 for communicating measurements acquired with the sensors 202 for analysis (e.g., by the data analyzer 30). The drill string 198 includes drill pipes coupled together at tool joints 210, and the drill string 198 can be moved through the annular preventer 180 such that the tool joints 210 pass through the closed packer 192. In at least some embodiments, the forces exerted by the joints 210 as they pass can be measured with embedded sensors (e.g., sensors 202) and their likely impact on the health and longevity of the packer 192 assessed. In the case of a subsea blowout preventer stack, such measurement and assessment may occur before the blowout preventer returns to the surface.

Changes in the loading (forces, stresses, strains) on the packer 192 (or on the donut 190) can be used to infer a change in radial dimension of the drill string associated with the tool joints 210, allowing detection of a tool joint 210 as it passes through the packer 192. The axial speed of the drill string 198 could be determined by measuring the elapsed time between successive tool joint detections in the blowout preventer and calculating speed using the measured time and a known distance between the tool joints. In other instances, the speed can be calculated in different ways. For example, the elapsed time over which the increased loading associated with a tool joint 210 passing through the packer 192 is measured by a sensor 202 can be compared with a known length of the tool joint 210 to determine the speed of travel. In another embodiment, the elapsed time between detection of increased stress as the tool joint 210 enters the packer 192 (or of decreased stress as the tool joint 210 exits the packer 192) by separate sensors 202 can be used to calculate speed. In one embodiment, an elapsed time since a tool joint 210 was detected passing through the blowout preventer is measured and the location of one or more tool joints 210 with respect to the blowout preventer is extrapolated from the calculated speed and the elapsed time. Knowledge of the distance between tool joints 210 of the drill string 198 would also allow the position of additional tool joints 210 to be determined (e.g., the position of tool joints above and below the blowout preventer).

Further, in embodiments in which the donut 190 or packer 192 have multiple sensors 202 provided at different axial locations, a timing differential in changes in stress detected by the sensors 202 can be used to detect the direction of travel of the drill string 198. For instance, an increase in stress detected first by an upper sensor 202 and then by a lower sensor 202 would be indicative of a tool joint 210 moving down through the packer 192. Conversely, increased stress detected first by a lower sensor 202 and then by an upper sensor 202 would indicate upward movement of the tool joint 210 through the packer 192.

Additionally, in some embodiments changes in loading on smart seals are used to control operation of blowout preventers or other components having the smart seals. For example, changes in loading measured by sensors embedded in a packer of a blowout preventer can be used to adjust closing pressure on the packer. In operation, a closing pressure on the packer 192 of the annular preventer 180 may be sufficient to seal the packer 192 about the drill string 198 between a pair of tool joints 210. Passage of tool joints 210 through the closed packer 192 increases loading on the packer 192, and the repeated passage of tool joints 210 through the packer 192 could negatively impact its health and longevity. While the loading can be measured and used to estimate the long-term effect of such forces, the detected changes in loading on the packer associated with the passing tool joints 210 could also or instead be used as feedback for the control of the blowout preventer.

In one embodiment, the closing pressure on the packer is reduced in response to a detected increase in the radial dimension of the drill string, which may be inferred from increased loading measured by an embedded sensor and correspond to entry of a tool joint 210 into engagement with the packer, as described above. Similarly, the closing pressure on the packer can be increased in response to a detected decrease in the radial dimension of the drill string associated with the exit of the tool joint out of engagement with the packer. Thus, forces on the packer can be selectively reduced to facilitate passage of tool joints and increase longevity of the packer.

In other embodiments, a variable bore ram includes one or more smart seals. A variable bore ram includes a packer that is similar to those used in both the pipe ram and annular blowout preventer. That is, it is put into contact with the object (e.g., a drill string) in the blowout preventer bore. A secondary mechanism then squeezes the packer in order to form a tighter seal against the object. By embedding one or more sensors (e.g., fiber-optic sensors or strain gauges) in the variable bore ram packer, it is possible to assess (e.g., from stress and strain data) the actual force applied by the packer to the object. This information could be used in several ways, including diagnosing problems with the secondary squeezing mechanism or with the closing system, as discussed above.

O-rings (as well as gaskets and other seals) can also be provided as smart seals having embedded sensors. O-rings are used throughout blowout preventers and their associated control systems. While it may be impractical to consider the use of such smart seals in every such case, there may be locations where it is desirable to monitor the health of O-ring seals. Many of the techniques described previously may apply equally well to O-rings as to the (generally) larger components discussed above. There will be a limit to how small the various optional constituent elements of a smart seal can be, however, and this in turn will dictate the possible functionality and therefore application of small O-rings. For example, a piezoelectric generator (for local power supply) or RFID device (for local communications) might be too large to be embedded in a small O-ring. In such situations, alternatives may be used, such as direct external wired connections for data and power.

As noted above, data acquired with sensors of the smart seals can be communicated to a processing system (e.g., data analyzer 30) in any suitable manner, which may include wired or wireless communication of data. In some embodiments, a wireless data receiver is positioned within the body of an oilfield component so as to be closer to smart seals within the oilfield component. In one embodiment depicted in FIG. 15, a blowout preventer 216 includes a ram 218 in a hollow body 220 having a bore 222. The blowout preventer 216 also includes a bonnet 224, through which a connecting rod 226 extends. A ram button 228 of the connecting rod 226 is received in the ram 218, allowing movement of the connecting rod 226 through the bonnet 224 to open and close the ram 218 in the preventer 216. The ram 218 includes a seal 230 (e.g., an elastomeric seal) having one or more embedded sensors for acquiring operating data for the seal. As generally described above, the acquired data may include physical operating data, such as measured forces and temperatures experienced by the seal 230.

Figure 15:
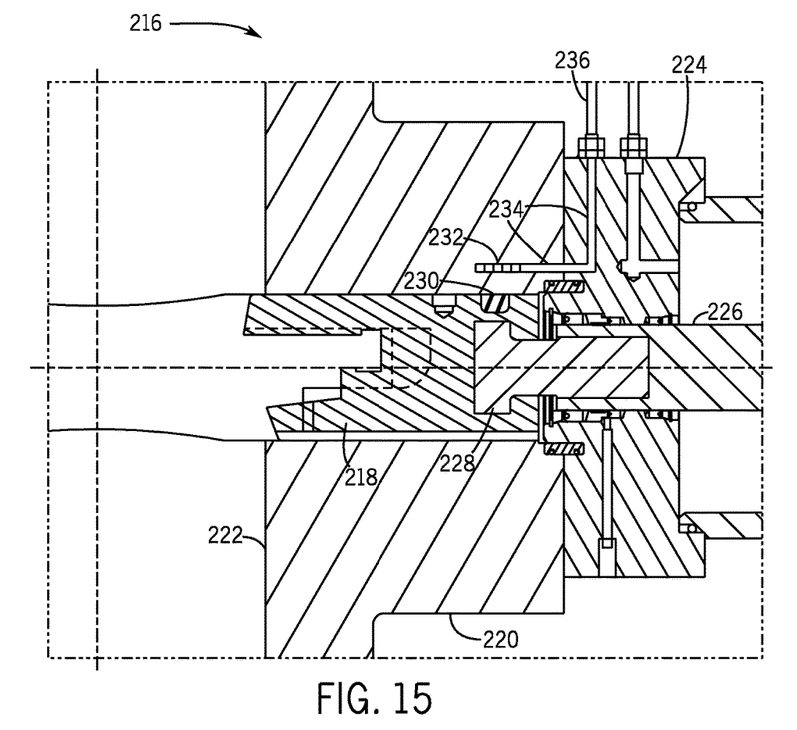
FIG. 15 depicts a blowout preventer with a data receiver embedded in a body of the blowout preventer to facilitate wireless communication with a sensor-enabled seal in accordance with one embodiment.

The depicted blowout preventer 216 also includes a data receiver 232 for wirelessly receiving data acquired with and transmitted from the seal 230. The data receiver 232 can take any suitable form, but in some instances is provided as a radio-frequency identification (RFID) reader embedded in the blowout preventer 216 and configured to receive data from an RFID tag in the seal 230. The communication range of an RFID system depends on numerous factors, including communication frequency, antenna size, power, surrounding environment, and whether the RFID tag to be read is active or passive. The receiver 232 may be positioned close to one or more smart seals to be monitored to facilitate communication. As shown in FIG. 15, the receiver 232 is embedded within the body 220 of the blowout preventer 216 above a ram cavity to provide a short communication path between the receiver 232 and the seal 230 when the ram 218 is in the open position. Passages 234 in the bonnet 224 and the main body of the blowout preventer 220 allow cabling to be routed to the embedded receiver 232. A wired connection 236 facilitates communication (e.g., power and data) between the receiver 232 and an external system (e.g., data analyzer 30).

In some instances, the communication range of the seal 230 and the RFID reader or other receiver 232 could be insufficient for reliable communication between these components when the ram 218 is moved from the open position shown in FIG. 15 to a closed position in the bore 222. In one such embodiment, data acquired by the embedded sensor of the seal 230 while the seal is in communication range of the receiver 230 are read in real-time, but the data acquired by the embedded sensor of the seal 230 while the seal 230 is out of communication range from the receiver 232 (e.g., when the ram 218 is moved away from its open position) are stored in a memory (e.g., a data storage device 68) within the seal 230. The data stored by the smart seal 230 can then be read with the receiver 232 when reliable communication can be established with the seal 230 (e.g., when the ram 218 moves back to the open position).

While certain examples of sensors able to measure forces and temperatures are described above, other sensors with different capabilities could be used in smart seals. For example, smart seals of certain embodiments include wear indicator sensors that can be used to detect wear or damage to the seals. In one embodiment depicted in FIG. 16, a ram packer 244 includes a non-conductive body 246 (e.g., an elastomeric body) between a pair of opposing plates 248. The ram packer 244 includes a pipe recess 252, facilitating sealing of the packer 244 (more specifically, a front surface 256 of the body 246) about a drill string or other object in a blowout preventer. A wear sensor 254 is embedded in the body 246 along the front, sealing surface 256. In the presently depicted embodiment, the wear sensor 254 is provided as an embedded wire extending between opposite ends of the packer 244 along the front surface 256, though the wear sensor 254 could take other forms in different embodiments.

Figure 16:
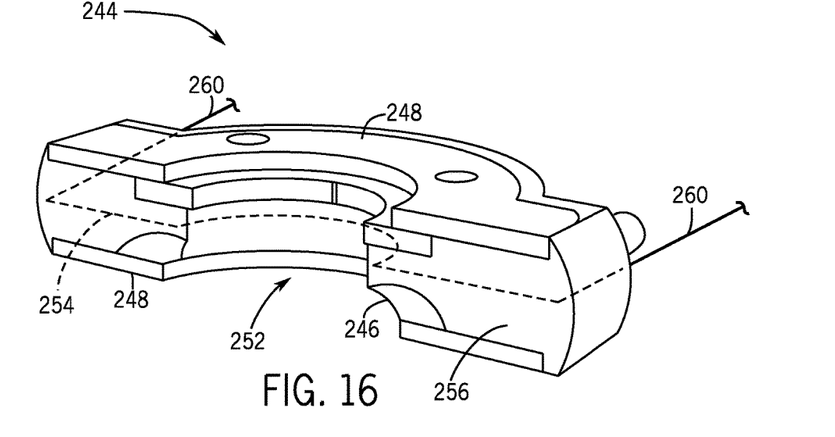
FIG. 16 depicts a ram packer having an embedded wear sensor in accordance with one embodiment.

The front surface 256 is a wear surface of the packer 244 and gradually erodes when deployed in a blowout preventer. The wear sensor 254 is positioned in the body 246 so as to enable detection of a predetermined amount of wear of the body 246 along the front surface 256. For example, the wear sensor 254 may be provided initially at a predetermined depth below the front surface 256. When the material of the body 246 along the front surface 256 wears by the predetermined amount, the sensor 254 is exposed. The exposed sensor 254 can come into contact with other objects (e.g., a metal drill string in the blowout preventer) to complete an electrical circuit when a ram carrying the packer 244 is closed. This electrical circuit can be monitored (e.g., by a data analyzer 30) to detect wear of the surface 256 down to the sensor 254, with detected electrical contact between the exposed sensor 254 and another object indicative that the predetermined amount of wear has, in fact, occurred.

The packer 244 is depicted in FIG. 16 with external leads 260 electrically coupled to the sensor 254 to facilitate communication with a data analyzer 30 or other external system. An electrical signal can be passed through the sensor 254 via the leads 260. In one embodiment, the data analyzer 30 can also test for continuity between the ends of the embedded wire of a sensor 254, with a loss of continuity indicating damage to the seal. This detected damage may serve as an early indication of impending seal failure. Although not shown in FIG. 16, it will be appreciated that additional sensors or other components may be embedded in the body 246 of the packer 244. Fiber-optic sensors or strain gauges, for example, could be embedded in the body 246 to detect temperatures, forces, and the like. A local power supply (e.g., a battery or piezoelectric generator) and an antenna for wireless communication could also be provided within the body 246. In such cases, the electrical testing could be performed with the local power supply with results transmitted wirelessly via the antenna, and the wired external leads 260 may be omitted.

Figure 17:
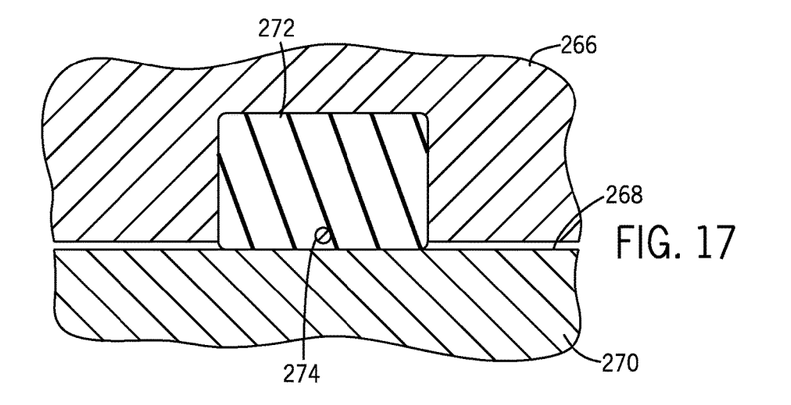
FIGS. 17-19 depict another seal having an embedded wear sensor in accordance with one embodiment.
Figure 18:
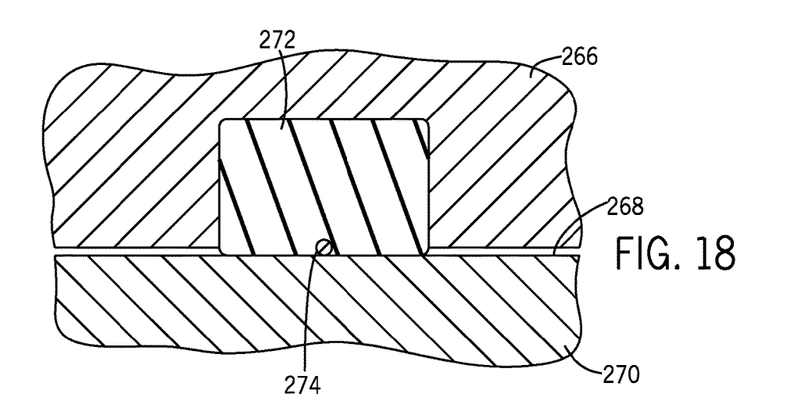
Figure 19:
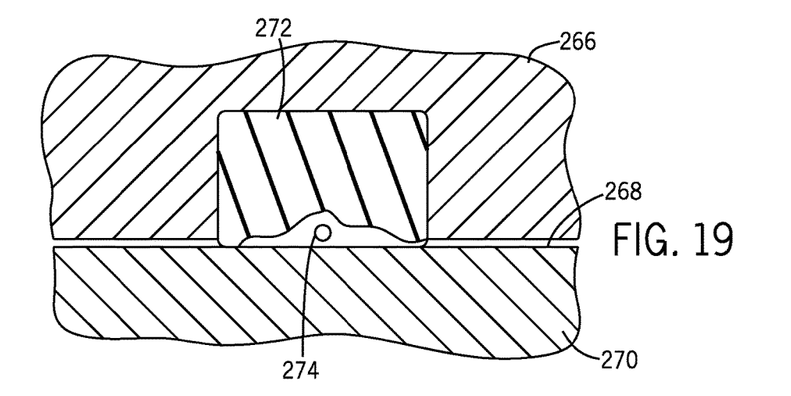

Although a ram packer is depicted in FIG. 16, wear sensors like those described above can be used in other seals as well. For example, a wire can be provided as a wear sensor in a different ram seal, an annular packer, a gasket, or an O-ring. By way of example, an elastomer seal 272 having a wire wear sensor 274 is depicted in FIGS. 17-19. The seal 272 is shown carried by a first component 266 and in sealing contact with a second component 270 along a surface 268. The first and second components may move relative to one another, causing wear on the seal 272 as it rubs along the surface 268. For instance, in one embodiment the first component 266 is a piston (e.g., an operating piston of a blowout preventer) and the second component 270 is a housing in which the piston reciprocates. In another embodiment, the second component 270 could be the moving component (e.g., a rod that moves along the seal 272 as the seal is held stationary by the first component 266). In FIG. 17, the wear sensor 274 is electrically isolated from the surface 268 of the component by the body of seal 272. Wear on the seal 272, however, can eventually expose the wear sensor 274 and allow electrical contact with the surface 268, as generally shown in FIG. 18. In some instances, damage to the sealing surface of the seal 272 can be detected using the wear sensor 274. For example, damage to the sealing surface (e.g., as shown in FIG. 19) can be indicated by a loss of continuity across the wire of the wear sensor 274, as described above.

Although certain examples of sensors and seals monitored with such sensors are described above, those skilled in the art will appreciate that the presently disclosed techniques can be used with other sensors and seals. For example, a wellhead assembly can include other seals with embedded sensors, such as seals in bonnets, connecting rods, flanges, electronics housings (e.g., a subsea electronics module housing), and components of a blowout preventer control system. Seals with condition sensors may also be used in other subsea or surface oilfield components (whether as part of or separate from a wellhead assembly), such as pumps, separators, generators, motors, gearboxes, processing equipment, production equipment, chokes, and valves. Further still, it will be appreciated that the present techniques discussed herein also have application in other industries that may benefit from monitoring the health and operating experience of seals and gaskets.

While the aspects of the present disclosure may be susceptible to various modifications and alternative forms, specific embodiments have been shown by way of example in the drawings and have been described in detail herein. But it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus comprising:
 a blowout preventer including a seal; and
 a blowout preventer seal-monitoring system including a sensor including a fiber-optic sensor and positioned within a body of the seal and a data analyzer having a processor and configured to monitor a condition of the seal through analysis of data received by the data analyzer from the sensor positioned within the body of the seal, wherein the data analyzer is configured to monitor the condition of the seal using measurements, acquired with the sensor, of temperature, pressure, or forces experienced by the seal.

2. The apparatus of claim 1, wherein the seal includes a power source embedded within the body of the seal and coupled to provide power to the sensor or to at least one other component embedded in the seal.

3. The apparatus of claim 1, wherein the seal includes an antenna that is embedded within the body of the seal and facilitates wireless communication of sensor data to the data analyzer.

4. The apparatus of claim 1, wherein the sensor positioned within the body of the seal includes a strain gauge.

5. The apparatus of claim 1, wherein the blowout preventer includes a ram-type blowout preventer having a ram including the seal.

6. The apparatus of claim 5, wherein the seal is a top seal of the ram or a ram packer of the ram.

7. The apparatus of claim 5, comprising a data receiver positioned to wirelessly receive data from the sensor within the body of the seal when the ram is in an open position in the blowout preventer.

8. The apparatus of claim 7, wherein the data receiver is a radio-frequency identification reader embedded in the blowout preventer.

9. The apparatus of claim 1, wherein the blowout preventer includes an annular blowout preventer having the seal.

10. The apparatus of claim 1, wherein the sensor is positioned in an elastomeric body of the seal.

11. The apparatus of claim 1, wherein the blowout preventer seal-monitoring system is configured to detect fluid ingress into the seal.

12. The apparatus of claim 1, wherein the sensor positioned within the body of the seal includes a wire embedded in the seal.

13. The apparatus of claim 12, wherein the wire is embedded in the seal along a wear surface of the seal.

14. The apparatus of claim 13, wherein the data analyzer is configured to detect electrical contact of the wire with another component in the event that the wire becomes exposed due to wear of the wear surface of the seal.

15. The apparatus of claim 12, wherein the data analyzer is configured to detect damage to the seal by measuring continuity between opposite ends of the wire.

16. An apparatus comprising:
 a seal having a non-conductive body; and
 a wear sensor embedded in the non-conductive body along a wear surface of the non-conductive body such that the wear sensor enables detection of a predetermined amount of wear of the non-conductive body at the wear surface, wherein the wear sensor is a wire sensor, the wear surface is a sealing surface of a ram packer, and the wire sensor extends along the sealing surface from one end of the ram packer to an opposite end of the ram packer.

17. The apparatus of claim 16, comprising a data analyzer coupled to the wire sensor and configured to detect the predetermined amount of wear of the non-conductive body at the wear surface by detecting electrical contact of the wire sensor with a different conductive component resulting from exposure of the wire sensor due to the predetermined amount of wear having occurred.

18. The apparatus of claim 17, wherein the data analyzer is configured to detect damage to the seal via continuity testing across the wire sensor.

19. A method comprising:
Acquiring physical operating data comprising temperature, pressure, or forces experienced by an elastomeric seal of an oilfield component with a sensor including a fiber-optic sensor embedded in an elastomeric sealing portion of the elastomeric seal;
processing the physical operating data acquired with the sensor embedded in the elastomeric sealing portion of the elastomeric seal; and
determining a condition of the elastomeric sealing portion via the processed physical operating data.

20. The method of claim 19, wherein acquiring physical operating data with the sensor includes measuring strain on the elastomeric seal during operation of the oilfield component.

21. The method of claim 19, wherein the elastomeric seal of the oilfield component is a blowout preventer seal, and processing the physical operating data acquired with the sensor embedded in the elastomeric sealing portion of the elastomeric seal includes processing the physical operating data acquired with the sensor embedded in the blowout preventer.

22. The method of claim 21, comprising wirelessly receiving the acquired physical operating data from the elastomeric seal.

23. The method of claim 22, wherein wirelessly receiving the acquired physical operating data from the elastomeric seal includes wirelessly receiving the acquired physical operating data from the elastomeric seal via a data receiver embedded within a body of a blowout preventer in which the blowout preventer seal is disposed.

24. The method of claim 23, wherein:
a ram of the blowout preventer includes the blowout preventer seal, and the ram moves away from an open position toward a closed position and then returns to the open position;
acquiring physical operating data with the sensor embedded in the elastomeric sealing portion of the elastomeric seal includes acquiring physical operating data from the sensor embedded in the blowout preventer seal while the ram is not in the open position; and
wirelessly receiving the acquired physical operating data from the elastomeric seal via the data receiver includes wirelessly receiving, while the ram is in the open position, the physical operating data that was acquired while the ram was not in the open position.

25. The method of claim 19, wherein the oilfield component is a subsea component, acquiring physical operating data with the sensor includes acquiring physical operating data with the sensor while the oilfield component is deployed underwater, and processing the physical operating data acquired with the sensor includes processing the physical operating data after retrieval of the oilfield component out of the water.

* * * * *